United States Patent [19]
Mizejewski

[11] Patent Number: 5,707,963
[45] Date of Patent: Jan. 13, 1998

[54] METHODS OF USING GROWTH INHIBITORY PEPTIDES

[75] Inventor: Gerald J. Mizejewski, Clifton Park, N.Y.

[73] Assignee: Health Research, Incorporated, Albany, N.Y.

[21] Appl. No.: 636,386

[22] Filed: Apr. 23, 1996

Related U.S. Application Data

[63] Continuation-in-part of PCT/US95/13848, Oct. 25, 1995, which is a continuation-in-part of Ser. No. 329,506, Oct. 26, 1994.

[51] Int. Cl.$^6$ ........................ A61K 38/17; C07K 14/435
[52] U.S. Cl. ........................... 514/12; 435/375; 530/324
[58] Field of Search ..................... 530/300, 350, 530/324; 435/69.1, 240.2, 325, 375; 514/2, 12, 17

[56] References Cited

U.S. PATENT DOCUMENTS

| | | | |
|---|---|---|---|
| 4,740,461 | 4/1988 | Kaufman | 435/68 |
| 4,753,879 | 6/1988 | Rosa et al. | 435/172.3 |
| 4,766,075 | 8/1988 | Goeddel et al. | 435/240.2 |
| 4,853,330 | 8/1989 | Goeddel et al. | 435/226 |
| 4,914,027 | 4/1990 | Knapp et al. | 435/69.6 |
| 5,096,696 | 3/1992 | Galanakis | 424/1.1 |
| 5,160,483 | 11/1992 | Postlethwaite | 424/85.1 |
| 5,206,164 | 4/1993 | Tecce et al. | 435/240.2 |
| 5,380,712 | 1/1995 | Ballance et al. | 514/12 |
| 5,384,250 | 1/1995 | Murgita | 435/69.1 |

OTHER PUBLICATIONS

Allen, et al., "Purification of alpha–fetoprotein from human cord serum with demonstration of its antiestrogenic activity," *Biochimica et Biophysica Acta*, 1202:135–142 (1993).
Bedo, et al., "Retinoic acid regulates growth hormone gene expression," *Nature*, 339:231–234 (May 18, 1989).
Bennett, et al., "Transformation of alpha–fetoprotein (AFP) to a negative regulator of estrogen–dependent growth by ligands of the steroid/thyroid hormone receptor superfamily," Abstract #1452, *Proceedings of the American Association for Cancer Research*, 34:224 (Mar. 1993).
Conti, et al., "Thyroid hormone effect on a α–fetoprotein and albumin coordinate expression by a human hepatoma cell line," *Biochimica et Biophysica Acta*, 1008:315–321 (1989).
Dietrich, "New aspects of steroid hormone dependent tumor growth," *Arch. Geschwulstforsch* 60(2):149–160 (1990).
Evans, "The Steroid and Thyroid Hormone Receptor Superfamily," *Science*, 240:889–895 (May 13, 1988).
Garreau, et al., "Phytoestrogrens: new ligands for rat and human α–fetoprotein," *Biochimica et Biophysica Acta*, 1094:339–345 (1991).
Gierthy, et al., "Correlation of in Vitro and in Vivo Growth Suppression of MCF–7 Human Breast Cancer by 2,3,7, 8–Tetrachlorodibenzo–p–dioxin," *Cancer Research*, 53:3149–3153 (Jul. 1, 1993).

Gorin, et al., "The Evolution of α–Fetoprotein and Albumin," *The Journal of Biological Chemistry*, 256(4):1954–1959 (Feb. 25, 1981).
Jacobson, et al., "Inhibition of Estrogen–dependent Breast Cancer Growth by a Reaction Product of α–Fetoprotein and Estradiol," *Cancer Research*, 50:415–420, (Jan. 15, 1990).
Jacobson, et al., "Estradiol–Induced Changes in Spectral and Biological Properties of Alpha–Fetoprotein," *Tumor Biology*, 11:104 (1990).
Keel, et al., "Purified Human Alpha Fetoprotein Inhibits Growth Factor–Stimulated Estradiol Production by Porcine Granulosa Cells in Monolayer Culture," *Endocrinology*, 130(6):3715–3717 (1992).
Keel, et al., "Purified human α–fetoprotein inhibits follicle–stimulating hormone–stimulated estradiol production by porcine granulosa cells in culture," *Molecular and Cellular Endocrinology*, 94:21–25 (1993).
Mizejewski, et al., "Stability of Complex Formation Between Estradiol and Murine Alpha–Fetoprotein," Abstract #7150, *Clinical Research*, (Spring 1977).
Mizejewski, et al., "Estradiol–activated α–fetoprotein suppresses the uterotropic response to estrogens," *Proc. Natl. Acad. Sci. USA*, 80:2733–2737 (May 1983).
Mizejewski, et al., "New Insights into AFP Structure and Function: Potential Biomedical Applications," in *Alpha–Fetoprotein and Congenital Disorders*, Mizejewski, et al., Eds., Academic Press, Inc. New York, N.Y., pp. 5–34 (1985).
Mizejewski, et al., "Studies of the Intrinsic Antiuterotropic Activity of Murine Alpha–Fetoprotein," *Tumour Biology*, 7:19–36 (1986).
Mizejewski, et al., "Alpha–Fetoprotein is a Dual Regulator of Growth in Estrogen–Responsive Tissues," in *Biological Activities of Alpha$_1$–Fetoprotein*, vol. I, Mizejewski, et al., Eds., CRC Press, Inc., Boca Raton, FL, pp. 71–82 (1987).
Mizejewski, et al., "AFP Modification of Biologic Response in Estrogen–Sensitive Tissues: Use of In Vivo and In Vitro Models," in *Biological Activities of Alpha$_1$–Fetoprotein*, vol. II, Mizejewski et al., Eds., CRC Press, Inc., Boca Raton, FL, pp. 59–74 (1989).
Mizejewski, et al., "Alpha–fetoprotein can regulate growth in the uterus of the immature and adult ovariectomized mouse," *J. Reprod. Fert*, 85:177–185 (1989).

(List continued on next page.)

Primary Examiner—Stephen Walsh
Assistant Examiner—Michael D. Pak
Attorney, Agent, or Firm—Jaeckle Fleischmann & Mugel, LLP

[57] ABSTRACT

The subject invention provides non-naturally occurring peptides capable of inhibiting growth factor-stimulated growth of cells. The peptide can be utilized to inhibit growth factor-stimulated growth, such growth factors including, for example, gonadotropins, peptide hormones, synthetic growth factors, and ligands, the ligand having a receptor that is a member of the steroid/thyroid hormone/vitamin receptor superfamily. Also provided are DNA sequences encoding the peptides and methods of producing and using the peptides.

12 Claims, No Drawings

OTHER PUBLICATIONS

Mizejewski, et al., "Separation of the Estrogen–Activated Growth–Regulatory Forms of Alpha–Fetoprotein in Mouse Amniotic Fluid," *Biology of Reproduction*, 42:887–898 (1990).

Mizejewski, "An Apparent Dimerization Motif in the Third Domain of Alpha–fetoprotein: Molecular Mimicry of the Steroid/Thyroid Nuclear Receptor Superfamily," *BioEssays*, 15:427–432 (1993).

Morinaga, et al., "Primary structures of human α–fetoprotein and its mRNA," *Proc. Natl. Acad. Sci. USA*, 80:4604–4608 (Aug. 1983).

Nishi, et al. "Estrogen–Binding Site of Rat Alpha–Fetoprotein," *Tumor Biology*, 14:234 (1993).

Nishi, et al., "Localization of the estrogen–binding site of α–fetoprotein in the chimeric human–rat proteins," *Proc. Natl. Acad. Sci. USA*, 88:3102–3105 (Apr. 1991).

Nunez, et al., "The Physicochemical and Biological Properties of Alpha–Fetoprotein Depend of its Ligand Environment," *J. Nucl. Med. Allied Sci.*, 33 (Suppl. to No. 3):18–26 (1989).

Rosebrock, et al., "Immunoprecipitation Assay of Alpha–fetoprotein Synthesis by Cultured Mouse Hepatoma Cells Treated with Estrogens and Glucocorticords," *Differentiation*, 19:168–178 (1981).

Savu, et al., "Mouse $\alpha_1$–Fetoprotein and Albumin," *The Journal of Biological Chemistry*, 256(18):9414–9418 (Sep. 25, 1981).

Sonnenschein, et al., "Growth Inhibition of Estrogen–Sensitive Tumor Cells in Newborn Rats. Probable Role of Alpha–Fetoprotein," *J. Natl. Can. Inst.*, 63(3):835–841 (Sep. 1979).

Sonnenschein, et al., "Age–Dependent Growth Inhibition of Estrogen–Sensitive Rat Mammary Tumors. Probable Role of Alpha–Fetoprotein," *J. Natl. Can. Instr.*, 64(5):1141–1146 (May 1980).

Sonnenschein, et al., "Growth Inhibition of Estrogen–Sensitive Rat Mammary Tumors. Effect of an Alpha–Fetoprotein–Secreting Hepatoma" *J. Natl. Can. Inst.*, 64(5):1147–1152 (May 1980).

Soto, et al., "Control of growth of estrogen–sensitive cells: Role for α–fetoprotein," *Proc. Natl. Acad. Sci. USA*, 77(4):2084–2087 (Apr. 1980).

Wahli, et al., "Superfamily of steroid nuclear receptors: positive and negative regulators of gene expression," *The FASEB Journal*, 5:2243–2249 (Jun. 1991).

Wan, et al., "The effects of retinoic acid on the expression of α–fetoprotein and albumin genes in rat hepatoma cell lines," *Differentiation*, 50:107–111 (1992).

METHODS OF USING GROWTH INHIBITORY PEPTIDES

This application is a continuation-in-part of PCT International Application No. PCT/U.S. Pat. No. 95/13848, filed Oct. 25, 1995, designating the United States of America, which is a continuation-in-part of U.S. Ser. No. 08/329,506, filed Oct. 26, 1994. The contents of each of these applications in their entireties are hereby incorporated by reference.

FIELD OF THE INVENTION

This invention is directed to a peptide, and more particularly to a non-naturally occurring peptide capable of inhibiting the growth of cells stimulated by growth factors. The invention also relates to DNA coding for this peptide and vectors and methods for producing the peptide.

BACKGROUND OF THE INVENTION

The nucleotide and amino acid sequences of mouse alpha-fetoprotein (AFP) and human AFP have been published (Gorin, M. B. et al., "The Evolution of α-Fetoprotein and Albumin", J Biol Chem 256:1954–1959 (1981); Morinaga, T. et al., "Primary Structures of human α-Fetoprotein and its mRNA", PNAS 80:4604–4608 (1983)). AFP is a glycoprotein produced during gestation, initially by the fetal yolk sac and then the fetal liver. AFP is a major serum protein constituent of the fetal plasma throughout gestation. However, upon parturition, the gene for AFP is repressed and its serum concentration diminishes to a negligible level. While a complete understanding of the physiological role of AFP is not yet available, the protein does display osmotic and carrier properties similar to albumin. Nevertheless, the reason for its unique existence during fetal development remains unclear.

Studies have shown that when AFP is incubated with a molar excess of the ligand estradiol ($E_2$), the AFP undergoes a change in conformation. This conformational change can be demonstrated spectrophotometrically by the method of difference spectrum (Jacobson, H. et al., "Estradiol-Induced Changes in Spectral and Biological Properties of Alpha-Fetoprotein", Tumour Biology 11:104 (1990)). In this transformed state, AFP inhibits growth of steroid stimulated tissues, including estrogen-stimulated breast cancer growth (Jacobson, H. I. et al., "Inhibition of Estrogen-dependent Breast Cancer Growth by a Reaction Product of α-Fetoprotein and Estradiol", Cancer Research 50:415–420 (1990)). This biological property is not present in native (untransformed) AFP. The anti-estrogenic growth activity was first demonstrated with murine AFP isolated from mouse amniotic fluid (Mizejewski, G. J. et al., "Estradiol-activated α-fetoprotein suppresses the uterotropic response to estrogens", PNAS 80:2733–2737 (1983); Mizejewski, G. J. et al., "Studies of the intrinsic Antiuterotropic Activity of Murine Alpha-Fetoprotein", Tumour Biology 7:19–36 (1986); Mizejewski, G. J. and A. S. Warner, "Alpha-fetoprotein can regulate growth in the uterus of the immature and adult ovariectomized mouse", J Reprod Fert 85:177–185 (1989)). In an attempt to understand this transformation and how AFP reacts with estrogen, the estrogen-binding site of alpha-fetoprotein in a chimeric human/rat protein was determined (Nishi, S. et al., "Localization of the estrogen-binding site of α-fetoprotein in the chimeric human-rat proteins", PNAS 88:3102–3105 (1991)).

Recently a procedure for purification of human AFP from pooled human cord sera was published (Allen, S.H.G. et al., "Purification of alpha-fetoprotein from human cord serum with demonstration of its antiestrogenic activity", Biochim Biophys Acta 1202:135–142 (1993)). Human AFP was similar to mouse AFP in its ability to be transformed by incubation with estradiol to an inhibitor of estrogen-stimulated growth of mouse uterus.

Estrogen is a growth factor that has a receptor which is a member of the steroid/thyroid hormone/vitamin receptor superfamily. Examples of other receptors in the superfamily include receptors for androgen, progesterone, vitamin-D, retinoic acid, retinol, tri-iodothyronine, glucocorticoids (such as hydrocortisone), and mineralcorticoid. (For a discussion of the receptor superfamily itself, see Evans, R. M., "The Steroid and Thyroid Hormone Receptor Superfamily", Science 240:889–895 (1988); Wahli, W. and Martinez, E., "Superfamily of steroid nuclear receptors: positive and negative regulators of gene expression", FASEB 5:2243–2249 (1991).)

The transformation of AFP by estrogen, and the presence of the receptor for estrogen in the superfamily, led researchers to explore the possibility that other ligands having receptors that are members of the superfamily could similarly transform AFP to an inhibitor of growth. Bennett et al. have shown that other ligands having receptors in the steroid/thyroid hormone/vitamin receptor superfamily also transform AFP to an inhibitor of estrogen-stimulated growth of cells (Bennett, J. A. et al., "Transformation of alpha-fetoprotein (AFP) to a negative regulator of estrogen-dependent growth by ligands of the steroid/thyroid hormone receptor superfamily", Abstract #1452, Proc. of Am. Assoc. for Cancer Research 34:244 (1993)).

Estrogen stimulates the growth of breast cancer cells. These other ligands discussed by Bennett et al. likewise stimulate the growth of other cells. For example, androgen stimulates the growth of prostate cancer cells. The purpose of the subject invention was to determine whether substances other than transformed full length AFP could inhibit the growth of cells, the growth of such cells being stimulated by growth factors, including those ligands whose receptors are members of the steroid/thyroid hormone/vitamin receptor superfamily.

SUMMARY OF THE INVENTION

It is thus an object of the subject invention to provide a peptide capable of inhibiting the growth of cells stimulated by growth factors. Preferably, the peptide of the subject invention is capable of inhibiting growth stimulated by ligands whose receptors are members of the steroid/thyroid hormone/vitamin receptor superfamily, more particularly steroid-stimulated growth such as by estrogen. The subject invention thus provides a non-naturally occurring peptide having an amino acid sequence consisting essentially of SEQ ID NO:8:

Leu Ser Glu Asp Lys Leu Leu Ala Xaa Gly Glu Gly Ala Ala Asp Ile Ile Ile Gly His Leu Xaa Ile Arg His Glu Met Thr Pro Val Ash Pro Gly Val.

The invention further provides an isolated fragment of this non-naturally occurring peptide, wherein the fragment consists essentially of at least six amino acids and wherein the fragment retains the ability to inhibit the growth of cells stimulated by growth factors.

In another embodiment, the peptide of the subject invention is a non-naturally occurring peptide having growth inhibitory activity similar to a second peptide, the second peptide having an amino acid sequence as shown in SEQ ID NO:1.

Having thus identified the peptides of the subject invention, expression systems are provided for production of the peptides using recombinant DNA technology. An expression vector (such as a plasmid) is thus provided by the subject invention which includes DNA encoding the non-naturally-occurring peptide, and which further includes suitable regulatory elements positioned within the expression vector relative to the DNA encoding the peptide so as to effect expression of the peptide in a suitable host cell. A host cell, such as a bacterial cell, is genetically modified to include the expression vector DNA and regulatory elements, and when the host cell is cultured the peptide is expressed and can be recovered. Isolated DNA molecules encoding the peptides of the subject invention, which can be contained in the plasmid, are also included in the scope of the subject invention.

The invention also provides a method of inhibiting growth factor-stimulated growth of cells. The method comprises selecting a sample having cells therein capable of growth factor-stimulated growth. These cells are contacted with the peptide of the subject invention, thereby inhibiting growth factor (i.e., asteroid such as estrogen)-stimulated growth of the cells.

DETAILED DESCRIPTION OF THE INVENTION

As used throughout this application, the term "consists essentially of" is used to indicate that the essential part of the peptide or DNA molecule is the indicated sequence. Non-essential nucleotides (for a DNA molecule) or amino acids (for a peptide) could be placed at the 5' and/or 3' ends of the molecule or peptide without affecting the growth inhibitory properties of the peptide.

The invention provides a non-naturally occurring peptide having an amino acid sequence consisting essentially of SEQ ID NO:8:

Leu Set Glu Asp Lys Leu Leu Ala Xaa Gly Glu Gly Ala Ala Asp Ile Ile Ile Gly His Leu Xaa Ile Arg His Glu Met Thr Pro Val Asn Pro Gly Val. In one embodiment, the Xaa residues at positions 9 and 22 in SEQ ID NO:8 are cysteine residues (as shown in SEQ ID NO:1). These positions can also be occupied by other suitable amino acids, such as alanine or serine, which have similar bulk and mass to cysteine, without affecting the growth inhibitory properties of the peptide. These cysteine residues (or other suitable amino acids) can also be methylated, amidated, or otherwise derivatized, as described below, without loss of growth inhibitory properties.

The invention further provides for the non-naturally occurring peptide to be labeled with a detectable marker. The marker could be a radioactive isotope, biotin, an element opaque to X-rays, or a paramagnetic ion. Radioactive isotopes are commonly used in medicine and are well known to those skilled in the art. Representative examples include indium-111, technetium-99m, and iodine-123. Biotin is a standard label which would allow detection of the biotin labeled peptide with avidin. Paramagnetic ions are also commonly used in medicine and include, for example, chelated metal ions of chromium (III), manganese (II), and iron (III). Using these detectable labels, the labeled peptide could be used as an imaging agent. Imaging can be done through any of the methods known in the art. These methods include, but are not limited to, X-ray, CAT scan, PET scan, NMRI, and fluoroscopy.

The invention further provides an isolated fragment of the non-naturally occurring peptide, wherein the fragment preferably consists essentially of at least six amino acids. Examples of isolated fragments include the peptides having amino acid sequences selected from the group consisting of SEQ ID NO:9, SEQ ID NO:2, SEQ ID NO:10, SEQ ID NO:3, SEQ ID NO:4, SEQ ID NO:5, SEQ ID NO:11, and SEQ ID NO:6. As indicated in the Sequence Listing provided at the end of this specification, SEQ ID NO:9 is identical to SEQ ID NO:2 except that the cysteine residue (present in SEQ ID NO:2) has been replaced with Xaa. As indicated above, the Xaa position could be occupied by other suitable amino acids such as alanine or serine without affecting the growth inhibitory properties of the peptide, and the amino acids could be methylated, amidated, or otherwise derivatized. Similarly, SEQ ID NO:10 is identical to SEQ ID NO:3 except that the cysteine residue (present in SEQ ID NO:3) has been replaced with Xaa, and SEQ ID NO:11 is identical to SEQ ID NO:6 except that the cysteine residues (present in SEQ ID NO:6) have been replaced with Xaa.

The fragments according to the subject invention have the same ability to inhibit the growth factor stimulated growth of cells. These fragments can also be labeled with a detectable marker, as discussed above in the context of the 34 amino acid peptide.

The invention further provides a non-naturally occurring peptide having growth inhibitory activity similar to a second peptide, the second peptide having an amino acid sequence as shown in SEQ ID NO:1. Suitable examples of such non-naturally occurring peptides include peptides having amino acid sequences selected from the group consisting of SEQ ID NO:8, SEQ ID NO:1, SEQ ID NO:9, SEQ ID NO:2, SEQ ID NO:10, SEQ ID NO:3, SEQ ID NO:4, SEQ ID NO:5, SEQ ID NO:11, and SEQ ID NO:6. These peptides are likewise capable of being labeled with a detectable marker.

As used herein in conjunction with a SEQ ID NO for an amino acid sequence, the terms "corresponding to" or "having" or "as shown in" or "consisting of" refer to an amino acid sequence which is substantially the same amino acid sequence or derivatives thereof. Amino acid additions, deletions, and/or substitutions which do not negate the ability of the resulting peptide to inhibit growth factor stimulated growth of cells are within the scope of an amino acid sequence corresponding to or having or as shown in or consisting of a particular amino acid sequence. Such additions, deletions, and/or substitutions can be, for example, the result of point mutations in the DNA encoding the amino acid sequence, such point mutations made according to methods known to those skilled in the art. Substitutions may be conservative substitutions of amino acids. Two amino acid residues are conservative substitutions of one another, for example, where the two residues are of the same type. In this regard, proline, alanine, glycine, serine, and threonine, all of which are neutral, weakly hydrophobic residues, are of the same type. Glutamine, glutamic acid, asparagine, and aspartic acid, all of which are acidic, hydrophilic residues, are of the same type. Another type of residue is the basic, hydrophilic amino acid residue, which includes histidine, lysine, and arginine. Leucine, isoleucine, valine, and methionine, all of which are hydrophobic, aliphatic amino acid residues, form yet another type of residue. Yet another type of residue consists of phenylalanine, tyrosine, and tryptophan, all of which are hydrophobic, aromatic residues. Further descriptions of the concept of conservative substitutions are given by French, S. and Robson, B., J Molecular Evolution 19:171–175 (1983), Taylor, W. R., J Theor Biol 119:205–218 (1986), and Bordo, D. and Argos, P., J Mol Biol 217:721–729 (1991), which are hereby incorporated by reference.

As further used herein, the term "corresponding to" or "having" or "as shown in" or "consisting of" when used in conjunction with a SEQ ID NO for an amino acid sequence is intended to cover linear or cyclic versions of the recited sequence (cyclic referring to entirely cyclic versions or versions in which only a portion of the molecule is cyclic, including, for example, a single amino acid cyclic upon itself), and is intended to cover derivative or modified amino acids within the recited sequence. For example, those skilled in the art will readily understand that an asparagine residue could be replaced with an ethylasparagine if an ethyl side chain is desired, a lysine residue could be replaced with a hydroxylysine if an OH side chain is desired, or a valine residue could be replaced with a methylvaline if a methyl side chain is desired. Amino acid sequences having a given SEQ ID NO are intended to encompass amino acid sequences containing these and like derivative or modified amino acids, as well as cyclic variations. Cyclic, as used herein, also refers to cyclic versions of the derivative or modified amino acids.

The peptides and fragments of the subject invention inhibit the growth factor stimulated growth of cells. They can be administered for this purpose alone or in combination with a suitable carrier as a composition. Compatible carriers include suitable pharmaceutical carriers or diluents. The diluent or carrier ingredients should be selected so that they do not diminish the therapeutic effects of the peptides or fragments of the present invention.

The compositions herein may be made up in any suitable form appropriate for the desired use; e.g., oral, parenteral, or topical administration. Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents such as starch and alginic acid, binding agents such as starch, gelatin, and acacia, and lubricating agents such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art. Examples of parenteral administration are intraventricular, intracerebral, intramuscular, intravenous, intraperitoneal, rectal, and subcutaneous administration.

Antibodies can also be raised to each of the peptides, and to the isolated fragments thereof. Antibodies of the subject invention include polyclonal antibodies and monoclonal antibodies which are specific for the peptides or isolated fragments thereof. It is known in the art that fragments of such antibodies can also be used to bind to the peptides or fragments thereof. These antibodies or fragments thereof can thus be used to detect the presence of a peptide in a sample (or to detect the presence of a fragment of a peptide), by contacting the sample with the antibody or fragment thereof. The antibody or fragment thereof binds to any peptide or fragment thereof present in the sample, forming a complex therewith. The complex can then be detected, thereby detecting the presence of the peptide or fragment thereof in the sample.

As used herein, a peptide or fragment thereof having an amino acid sequence identified by a SEQ ID NO, or having an amino acid sequence consisting essentially of a sequence identified by a SEQ ID NO, or a nucleic acid molecule encoding a peptide or fragment encoding an amino acid sequence identified by a SEQ ID NO, or encoding an amino acid sequence consisting essentially of a sequence identified by a SEQ ID NO, has an amino acid or nucleotide sequence which is at least 90% homologous to the amino acid or nucleotide sequence shown in the SEQ ID NO.

While the amino acid or nucleotide sequence is at least 90% homologous, nucleotide and/or amino acid identity is not required. As should be readily apparent to those skilled in the art, various nucleotide substitutions are possible which are silent mutations (i.e. the amino acid encoded by the particular codon does not change). It is also possible to substitute a nucleotide which alters the amino acid encoded by a particular codon, where the amino acid substituted is a conservative substitution (i.e. amino acid "homology" is conserved). It is also possible to have minor nucleotide and/or amino acid additions, deletions, and/or substitutions in the peptide or fragment nucleotide and/or amino acid sequences which do not alter the ability of the peptide or fragment to inhibit the growth factor stimulated growth of cells.

As defined herein, the peptides of the subject invention are intended to cover non-naturally occurring peptides having growth inhibitory activity similar to the peptide represented by SEQ ID NO:1. Growth inhibitory activity can be determined by any suitable means known in the art. For example, inhibition of estrogen-stimulated growth can be assayed as discussed in Examples 2 and 3 below. Inhibition of diethylstilbestrol (DES)-stimulated growth can be assayed as discussed in Example 4. Inhibition of hydrocortisone (HC)-stimulated growth can be assayed as discussed in Example 5, and inhibition of human chorionic gonadotropin (HCG)-stimulated growth can be assayed as discussed in Example 6.

The peptides of the subject invention thus include those consisting essentially of SEQ ID NO:8 or SEQ ID NO:1, as well as those consisting essentially of fragments of SEQ ID NO:8 or SEQ ID NO:1 (for example, SEQ ID NO:9, SEQ ID NO:2, SEQ ID NO:10, SEQ ID NO:3, SEQ ID NO:4, SEQ ID NO:5, SEQ ID NO:11, and SEQ ID NO:6) having such growth inhibitory activity. Furthermore, substitutions, additions, deletions, and other alterations of the DNA or amino acid sequences described herein that result in a peptide with the capability of inhibiting such growth factor-stimulated growth of cells are intended to be covered herein. This would include naturally-occurring allelic variations and recombinant variations, such as site-directed mutagenesis.

As shown below, the peptide according to the subject invention can be modified by labeling the peptide, for example with biotin, without affecting the ability of the peptide to inhibit growth factor stimulated growth of cells. Furthermore, the cysteine residues can be blocked by methylation or amidation without affecting the inhibitory properties. Therefore, these cysteine residues could also be replaced with other suitable amino acids such as alanine or serine.

Growth factors, as used herein, include cell signalling molecules which mediate cellular multiplication and proliferation. Such growth factors include, for example, the family of gonadotropins (including HCG, follicle-stimulating hormone (FSH), luteinizing hormone (LH), and thyroidstimulating hormone (TSH)), naturally-occurring peptide hormones (such as kinins, which include angiotensin, neuromedin, neurotensin, bradykinin, and substance P), ligands whose receptors are members of the steroid/thyroid hormone/vitamin receptor superfamily (for example, estrogen, androgen, progesterone, vitamin-D, retinoic acid, retinol, tri-iodothyronine, glucocorticoid, and mineralcorticoid), and synthetic growth factors such as DES (a synthetic estrogen) and phorbol esters.

Isolated DNA molecules are also provided consisting essentially of DNA coding for a non-naturally occurring peptide, the peptide having an amino acid sequence consisting essentially of SEQ ID NO:8:
Leu Ser Glu Asp Lys Leu Leu Ala Xaa Gly Glu Gly Ala Ala Asp Ile ile Ile Gly His Leu Xaa Ile Arg His Glu Met Thr Pro Val Ash Pro Gly Val.

In one embodiment, the DNA molecule encodes a non-naturally occurring peptide having an amino acid sequence consisting essentially of SEQ ID NO:1.

Isolated fragments of the DNA molecules are also provided, wherein the fragment preferably encodes at least six amino acids. Examples of such fragments include fragments encoding an amino acid sequence consisting essentially of a sequence selected from the group consisting of SEQ ID NO:9, SEQ ID NO:2, SEQ ID NO:10, SEQ ID NO:3, SEQ ID NO:4, SEQ ID NO:5, SEQ ID NO: 11, and SEQ ID NO:6.

An isolated DNA molecule is further provided consisting essentially of DNA coding for a non-naturally occurring peptide, the peptide having growth inhibitory activity substantially similar to a second peptide. The second peptide has an amino acid sequence as shown in SEQ ID NO:1. Preferably, the non-naturally occurring peptide has an amino acid sequence selected from the group consisting of SEQ ID NO:8, SEQ ID NO:1, SEQ ID NO:9, SEQ ID NO:2, SEQ ID NO:10, SEQ ID NO:3, SEQ ID NO:4, SEQ ID NO:5, SEQ ID NO:11, and SEQ ID NO:6.

The peptide of the present invention is preferably produced in purified form by conventional techniques using synthetic peptide chemistry in a peptide synthesizer or using recombinant DNA technology. In recombinant DNA technology, typically the peptide of the present invention is secreted into the growth medium of recombinant E. coli. To isolate the peptide, the E. coli host cell carrying a recombinant plasmid is propagated, homogenized, and the homogenate is centrifuged to remove bacterial debris. The supernatant is then subjected to sequential ammonium sulfate precipitation. The fraction containing the peptide of the present invention is subjected to gel filtration in an appropriately sized dextran or polyacrylamide column to separate the peptides. If necessary, the peptide fraction may be further purified by HPLC.

Fragments of the peptide can be obtained by cutting the entire 34 amino acid peptide with suitable enzymes, such as trypsin or restriction enzymes. Alternatively, fragments can be synthesized using synthetic peptide chemistry.

The DNA molecule encoding the peptide can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted peptide-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccinia virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/– or KS +/– (see "Stratagene Cloning Systems" Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," Gene Expression Technology 185 (1990), which is hereby incorporated by reference), and any derivatives thereof. Recombinant molecules can be introduced into cells via transformation, particularly transduction, conjugation, mobilization, or electroporation. The DNA sequences are cloned into the vector using standard cloning procedures in the art, as described by Maniatis et al., *Molecular Cloning: A Laboratory Manual*, Cold Springs Laboratory, Cold Springs Harbor, N.Y. (1982), which is hereby incorporated by reference.

A variety of host-vector systems may be utilized to express the peptide-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promotors differ from those of procaryotic promotors. Furthermore, eucaryotic promotors and accompanying genetic signals may not be recognized in or may not function in a procaryotic system, and, further, procaryotic promotors are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosomal binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, Methods in Enzymology, 68:473 (1979), which is hereby incorporated by reference.

Promotors vary in their "strength" (i.e. their ability to promote transcription). For the purposes of expressing a cloned gene, it is desirable to use strong promotors in order to obtain a high level of transcription and, hence, expression of the gene. Depending upon the host cell system utilized, any one of a number of suitable promotors may be used. For instance, when cloning in *E. coli*, its bacteriophages, or plasmids, promotors such as the T7 phage promoter, lac promotor, trp promotor, recA promotor, ribosomal RNA promotor, the $P_R$ and $P_L$ promotors of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promotors produced by recombinant DNA or other synthetic DNA techniques may be used to provide for transcription of the inserted gene.

Bacterial host cell strains and expression vectors may be chosen which inhibit the action of the promotor unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires a Shine-Dalgarno (SD) sequence about 7–9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding the peptide of the subject invention has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, and the like.

Having thus identified and produced the peptides and fragments according to the subject invention, a method of inhibiting growth factor-stimulated growth of cells is provided. The method comprises selecting a sample having cells therein capable of growth factor-stimulated growth, and contacting the sample with the peptide or fragment of the subject invention. This inhibits growth factor-stimulated growth of the cells. Cells as used herein encompasses a wide range of cells that can be stimulated in their growth by the growth factors, including cancerous cells such as breast cancer cells (whose growth is stimulated by estrogen) and prostate cancer cells (whose growth is stimulated by androgen).

The details of the subject invention are disclosed more fully below in the context of experimental details.

Example 1

A 34-amino acid peptide was synthesized in an Applied Biosystems 431A peptide synthesizer (Foster City, Calif.), the peptide consisting of the following amino acid sequence, SEQ ID NO: 1:

Leu Ser Glu Asp Lys Leu Leu Ala Cys Gly Glu Gly Ala Ala Asp Ile ile Ile Gly His Leu Cys Ile Arg His Glu Met Thr Pro Val Ash Pro Gly Val.

The synthesized 34-mer peptide was analyzed by mass spectrometry and found to contain the predicted molecular mass (3,573 Daltons). A subsequent analysis of the crude peptide by circular dichroism revealed 7% alpha-Helix, 43% beta sheets, and 45% random (coil) turns. The crude peptide was further purified by HPLC to 99.9% purity, and the amino acid composition of the HPLC-purified peptide revealed the presence of all the designated amino acids (except proline and cysteine that cannot be measured). Thus, the major component in the crude synthetic preparation contained the amino acid composition of the peptide intended.

The 34-mer peptide, designated the Growth Inhibitory Peptide (GIP), was subsequently tested for its biological activity in two separate bioassays for inhibition of estrogen-stimulated growth (an in vivo bioassay measuring an estrogen-induced increase in wet weight of the immature mouse uterus in a 24-hour determination; and an in vitro assessment of estrogen-induced foci formation by human MCF-7 breast cancer cells), as well as separate bioassays for inhibition of DES-stimulated growth (an in vivo bioassay measuring a DES-induced increase in wet weight of the immature mouse uterus); inhibition of hydrocortisone-stimulated growth (an in vivo bioassay measuring a hydrocortisone-induced increase in wet weight of the immature mouse spleen); and inhibition of HCG-stimulated growth (an in vivo bioassay measuring an HCG-induced increase in wet weight of the immature mouse ovary). In all assay results for immature mice, each experiment represents data from five individual mice, and in all assay results for adult mice, each experiment represents data from three individual mice.

Example 2

An in vivo wet weight bioassay measuring inhibition of estrogen-stimulated growth of uteri was performed. The procedure of Mizejewski et al. was used for the wet weight assay (see Mizejewski, G. J. et al. (1983); Mizejewski, G. J. et al. (1986); Mizejewski, G. J. and A. S. Warner (1989); Mizejewski, G. J. et al., "Separation of the Estrogen-Activated Growth-Regulatory Forms of Alpha-Fetoprotein in Mouse Amniotic Fluid," Biol of Reprod 42:887–898 (1990); and Allen, S.H.G. et al. (1993)).

Briefly, the synthesized powdered peptide was reconstituted in saline (1 mg/ml) to form a stock solution of the GIP. The stock solution was appropriately diluted to provide dosages of 25 to 100 ng/mouse. 0.1 ml of the appropriately diluted GIP was injected intraperitoneally into 15–18 day old Nya:NYLAR female mice. Control mice were injected with saline or other peptides, including a peptide encoded by a portion of the amino acid sequence of albumin and a random 34 amino acid peptide. 1 hour after this first injection, an estrogen challenge of 0.5 micrograms of $E_2$ in 0.1 ml saline was given to determine the change in uterine responsiveness to $E_2$ resulting from exposure to the first injection. 23 hours after the second injection, uteri were dissected, trimmed free of connective tissue and immediately weighed. The uterine wet weights were normalized to mouse body weight (mg uterine weight/g of body weight) to compensate for differences in body weight among litters of the same age. Percent inhibition of estrogen-stimulated uterine growth was calculated as described by Mizejewski et al. (1983).

The results of the wet weight assay for GIP are summarized in Table 1. These data indicate that the met peptide (GIP) gave inhibition of 33–79% of estrogen-stimulated growth. This inhibition was similar and/or exceeded inhibition of estrogen-stimulated growth obtained with the full-length transformed AFP molecule (20–40% inhibition) (see references cited). The bioassay data for the immature mice was confirmed again on about forty additional repeats and at least ten additional repeats were performed using adult female mice.

The most effective dose of GIP to produce 30–40% growth inhibition in the immature uterus was determined to be 50ng/mouse, thus being 5-fold more potent than the full-length transformed AFP molecule. As discussed previously, $E_2$ activation of full-length AFP in a test tube prior to inoculation (resulting in transformed AFP) is necessary for the full-length protein to have this inhibitory effect, but proved unnecessary for the GIP (with activity demonstrable at 100ng/mouse) provided the mouse contains the circulating ligand (estrogen). Furthermore, it was demonstrated that GIP was active in adult cycling mice both with and without the addition of purified human full-length AFP. Finally, it was demonstrated that other control peptides, a 34-mer anomalous control peptide and a peptide from the carboxy terminal half of bovine serum albumin, showed no effect whatever over the same dose titration range in the immature mouse uterus.

Example 3

In an in vitro bioassay, the MCF-7 focus assay was used for preliminary evaluation of the GIP preparation for both estrogenicity and antiestrogenicity. One of the major consequences of human estrogen exposure is induction of cell proliferation and subsequent structural rearrangement of the acini, a process based on the interactions of multiple estrogen dependent gene expressions. The MCF-7 human breast epithelial cell line derived from an adenocarcinoma has been used extensively as a model of estrogen dependent breast cancer, and MCF-7 cultures exhibit estrogen dependent enhanced cell proliferation in vitro and in vivo using xenografts. The estrogen dependent MCF-7 cell proliferation is primarily a postconfluent event which leads to development of multicellular aggregates (foci). These studies have characterized the estrogen dependency of focus development in MCF-7 cultures and demonstrated the usefulness of this system as an assay for estrogenic activity or, by challenging an estrogen stimulation, the antiestrogenic efficacy of a substance. The procedure of Gierthy et al. was used for the MCF-7 assay of the GIP (see Gierthy, J. F. et al., "Correlation of in Vitro and in Vivo Growth Suppression of MCF-7 Human Breast Cancer by 2,3,7,8-Tetrachlorodibenzo-p-dioxin" Cancer Research 53:3149–3153 (1993)).

Briefly, stock MCF-7 cells were suspended in medium (see Gierthy, J. F. et al. 1993) after treatment with trypsin (0.25%) and seeded into 24-well plastic tissue culture plates. The MCF-7 cells were seeded (2 cm²/well) at a density of b $10^5$ cells/well in 1 ml of medium, and incubated at 37° C. in a humidified atmosphere containing 5% $CO_2$. The cultures were refed at 24 hours and every 4–5 days thereafter with 2 ml medium supplemented with $1 \times 10^{-9}$M 17β-estradiol, a concentration which induces maximum focus development, and various concentrations of GIP ($10^{-8}$M–$10^{-13}$M) in nonestrogenic $DC_5$ medium and estrogenic $DF_5$ medium which contains high levels of bovine alpha-fetoprotein (5% fetal bovine serum supplemented). After 14 days the cultures were fixed with formalin in pH 7.4 buffer (see Gierthy, J. F. et al. 1993) and stained with 1% rhodamine B. Foci were counted by using an automated colony counter modified to magnify the image of the microscopic multicellular foci. The foci retained the red rhodamine B stain to a greater extent than did surrounding monolayer cells, affording appropriate contrast for enumeration.

The results of the MCF-7 assay for GIP are summarized in Table 2. Results were confirmed with additional repeats and indicate that GIP was inhibitory to the $DF_5$ induced foci development to a maximum of 74% over a GIP concentration range of $10^{-10}$ to $10^{-13}$M. It was also found that higher concentrations of GIP were estrogenic, i.e., induced foci development, in the nonestrogenic $DC_5$ environment in a dose responsive manner starting at $10^{-8}$M. Therefore, GIP exhibits a biphasic response which is antiestrogenic at low concentrations and estrogenic at higher concentrations.

Example 4

An in vivo wet weight bioassay measuring inhibition of diethylstilbestrol (DES)-stimulated growth was also performed. The procedure of Mizejewski et al. (see previous citations) was used for the wet weight assay. The applicability of the wet weight bioassay for measuring DES-stimulated growth of uteri is disclosed by Korach, K. S. et al., "Estrogenic activity in vivo and in vitro of some diethylstilbestrol metabolites and analogs", Proc Natl Acad Sci USA 75:468–471 (1978).

Briefly, the synthesized powdered peptide was reconstituted in saline (1 mg/ml) to form a stock solution of the GIP. The stock solution was appropriately diluted to provide dosages of 10 ng to 100 µg/mouse. 0.1 ml of the appropriately diluted GIP was injected intraperitoneally into 15–18 day old Nya:NYLAR female mice. Control mice were injected with saline. 1 hour after this first injection, a DES challenge of 0.5 micrograms of DES in 0.1 ml saline was given to determine the change in uterine responsiveness to DES resulting from exposure to the first injection. 23 hours after the second injection, uteri were dissected, trimmed free of connective tissue and immediately weighed. The uterine wet weights were normalized to mouse body weight (mg uterine weight/g of body weight) to compensate for differences in body weight among litters of the same age. Percent inhibition of DES-stimulated uterine growth was calculated as described by Mizejewski et al. (1983).

The results of the wet weight assay are summarized in Table 3. These data indicate that the 34-mer peptide (GIP) gave inhibition of DES-induced growth in a range of 14–27%. The bioassay data for the immature mice was confirmed again on three additional repeats and a further repeat was performed using adult female mice.

The most effective dose of GIP which produced 27% growth inhibition in the immature uterus was determined to be 10ng/mouse.

Example 5

An in vivo wet weight bioassay measuring inhibition of hydrocortisone (HC)-stimulated growth of the spleen was also performed. The procedure of Mizejewski et al. (see previous citations) was used for the wet weight assay. The applicability of the wet weight bioassay for measuring HC-stimulated growth of the spleen is disclosed by el-Fouhil, A. F. and Turkall, R. M., "Effect of alternate-day hydrocortisone therapy on the immunologically immature rat. I: Effect on blood cell count, immunoglobulin concentrations, and body and organ weights", Toxicologic Pathology 21(4):377–382 (1993).

Briefly, the synthesized powdered peptide was reconstituted in saline (1 mg/ml) to form a stock solution of the GIP. The stock solution was appropriately diluted to provide dosages of 500 ng to 100 µg/mouse. 0.1 ml of the appropriately diluted GIP was injected intraperitoneally into 15–18 day old Nya:NYLAR female mice. Control mice were injected with saline. 1 hour after this first injection, an HC challenge of 0.5 micrograms of HC in 0.1 ml saline was given to determine the change in spleenic responsiveness to HC resulting from exposure to the first injection. 23 hours after the second injection, spleens were dissected, trimmed free of connective tissue and immediately weighed. The spleenic wet weights were normalized to mouse body weight (mg spleenic weight/g of body weight) to compensate for differences in body weight among litters of the same age. Percent inhibition of HC-stimulated spleenic growth was calculated as described by Mizejewski et al. (1983).

The results of the wet weight assay are summarized in Table 4. These data indicate that the 34-mer peptide (GIP) gave inhibition of HC-induced growth in a range of 24–100%. The bioassay data for the immature mice was confirmed again on one additional repeat.

The most effective dose of GIP which produced 100% growth inhibition in the immature spleen was determined to be 1.0 µg/mouse.

Example 6

An in vivo wet weight bioassay measuring inhibition of human chorionic gonadotropin (HCG)-stimulated growth of the ovary was performed. The procedure of Mizejewski et al. (see previous citations) was used for the wet weight assay. The applicability of the wet weight bioassay for measuring HCG-stimulated growth of the ovary is disclosed by Mizejewski, G. J., "Human Chorionic Gonadotrophin: Comparative Studies of Ovarian Uptake In Mammals", Comp Biochem Physio 52A:29–34 (1975).

Briefly, the synthesized powdered peptide was reconstituted in saline (1 mg/ml) to form a stock solution of the GIP. The stock solution was appropriately diluted to provide dosages of 10ng to 100 µg/mouse. 0.1 ml of the appropriately diluted GIP was injected intraperitoneally into 15–18 day old Nya:NYLAR female mice. Control mice were injected with saline. 1 hour after this first injection, an HCG challenge of 2.8 I.U. of HCG in 0.05 ml saline was given to determine the change in ovarian responsiveness to HCG resulting from exposure to the first injection. 23 hours after the second injection, ovaries were dissected, trimmed free of connective tissue and immediately weighed. The ovarian wet weights were normalized to mouse body weight (mg ovarian weight/g of body weight) to compensate for differences in body weight among litters of the same age. Percent inhibition of HCG-stimulated ovarian growth was calculated as described by Mizejewski et al. (1983).

The results of the wet weight assay are summarized in Table 5. These data indicate that the met peptide (GIP) gave inhibition of HCG-induced growth in a range of 22–100%. The bioassay data for the immature mice was confirmed again on two additional repeats and a further repeat was performed using adult female mice.

The most effective dose of GIP which produced 100% growth inhibition in the immature ovary was determined to be 1 µg/mouse.

Based on these findings, one concludes that the growth inhibitory peptide of the subject invention, when diluted 2,000-fold or more, produces a 30–40% inhibition of estrogen-stimulated growth in the immature mouse uterus, 80% in the adult, and 60–70% inhibition at $10^{-10}$ to $10^{-13}$M peptide concentration in the MCF-7 cell culture assays. Various beneficial characteristics of GIP make it superior to native, full-length transformed AFP as an inhibitor of estrogen-induced growth. One characteristic is that the GIP is used without the need for transformation with a ligand, such as estradiol, assuming there is some estrogen present in the assay system. Furthermore, the 34 amino acid sequence is practical as an inhibitor of growth factor-stimulated growth in general because it can be readily produced with a peptide synthesizer or using recombinant DNA techniques. Additionally, unlike the full-length transformed human AFP preparations, the GIP retains its inhibitory activity in the lyophilized state for at least twelve (12) months. In contrast, the transformed human AFP retains activity for one week or less. Thus, GIP offers significant advantages as an inhibitor of growth factor-stimulated growth over transformed, full-length human alpha-fetoprotein.

Example 7

The full length 34 amino acid peptide having SEQ ID NO:1 was cut with trypsin to generate three fragments. The 5' fragment has SEQ ID NO:5, the central fragment has SEQ ID NO:6, and the 3' fragment has SEQ ID NO:7. Fragments of the full-length peptide were also synthesized in a peptide synthesizer, resulting in the 5' fragment having SEQ ID NO:2, the central fragment having SEQ ID NO: 3, and the 3' fragment having SEQ ID NO:4. Each of these fragments was then tested for its ability to inhibit the growth factor stimulated growth of cells.

Two separate bioassays for inhibition of estrogen-stimulated growth were used. The first was an in vivo bioassay measuring an estrogen-induced increase in wet weight of the immature mouse uterus in a 24-hour determination. Dosages of peptide fragments ranged from 10 to 100 ng, and the %inhibition given in Table 6 represents the peak assay point of the dilution series. As indicated in Table 6, the percent growth inhibition ranged from 19% for the fragment having SEQ ID NO:6 to 41% for the fragment having SEQ ID NO:4. Note that the fragment having SEQ ID NO:7 gave no detectable growth inhibition, and therefore the probable minimum fragment length is about 6 amino acids (the fragment having SEQ ID NO:7 was 5 amino acids in length). This data indicates that fragments of the full length 34 amino acid peptide also exhibit the capability to inhibit the growth factor stimulated growth of cells.

A second assay was also used to assess the percent of inhibition for the various fragments. This data is summarized in Tables 7 and 8. Briefly, the data represents an in vivo assay used to measure the inhibition of growth of the mouse mammary tumor 6WI-1 in a mouse. The procedure of Parsons et al. was used in this assay (see Parsons et al., Cancer investigation 4(2):109–126 (1986)). The mouse mammary tumor 6WI-1 normally kills animals within 12–15 days. In this assay, the tumor cells were injected into the body cavity of live mice. Table 7 represents data for injection of $1.1–4.0 \times 10^6$ tumor cells per mouse, and Table 8 represents data for injection of 0.3–1.0×10⁶ tumor cells per mouse. The inhibition of tumor growth is indicated by percentage. The data again indicates that the fragments of the full length 34 amino acid peptide exhibit the capability to inhibit the growth factor stimulated growth of cells. Unless otherwise indicated, the dose of peptide or peptide fragment was injected into the body cavity of the mice on day 1 and every day for 15 days. Percent inhibition was measured on day 15.

Example 8

Various alterations to the 34 amino acid peptide were made to test the ability of the altered peptide to inhibit growth factor stimulated growth of cells. In one altered peptide, the cysteine residues in the 34 amino acid peptide were blocked by methylation. This methylated peptide provided 30–50% inhibition of estrogen-stimulated growth of uteri. In another alteration, the cysteine residues were blocked by amidation. This altered peptide provided 25–35% inhibition of estrogen-stimulated growth of uteri. Accordingly, these results show that blockage of the cysteine residues does not adversely affect the properties of the peptide, and therefore the cysteine residues could be replaced by other amino acids without adversely affecting the properties of the peptide. In fact, the presence of the cysteine residues can cause the peptide to be somewhat unstable in liquid solution after a couple days. This issue of stability can be addressed by storing the peptide as a powder, or by complexing the cysteine residues to stabilize the peptide. The cysteine residues can be complexed as indicated above, such as by methylation or amidation, and the resulting peptide can be stored as a liquid for a longer period of time than the unaltered peptide.

The 34 amino acid peptide was also labeled with biotin to study the effect of such labeling on the properties of the peptide, and it was found that the biotin-labeled peptide was able to inhibit the estrogen-stimulated growth of uteri. The peptide was labeled by covalently binding biotin to one of the cysteine residues of the peptide.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

In Vivo Wet Weight Bioassay Results
(Estrogen-Stimulatd Growth of Uteri)

| Experiment # | Assay | Dose Per Mouse | Percent Growth Inhibition |
|---|---|---|---|
| 1 | immature mouse uterus | 25 ng | 33 |
| 2 | immature mouse uterus | 50 ng | 38 |
| 3 | immature mouse uterus | 50 ng | 37 |
| 4 | immature mouse uterus | 100 ng | 35 |
| 5a | immature mouse uterus | 50 ng | 37 |
| 5b | - added human AFP | 25 ng | 42 |
| 6a | adult mouse uterus | 25 ng | 66 |
| 6b | - added human AFP | 100 ng | 79 |

TABLE 2

In Vitro MCF-7 Assay Results

| Experiment # | Assay | Peptide Molarity | Percent Foci Inhibition |
|---|---|---|---|
| 1 | MCF-7 Cell Culture | $10^{-7}$–$10^{-12}$ | 60–70 |
| 2a | MCF-7 Cell Culture | $10^{-11}$–$10^{-13}$ | 60–74 |
| 2b | - added human AFP | $10^{-12}$ | 40 |
| 3 | MCF-7 Cell Culture | $10^{-11}$–$10^{-13}$ | 50–60 |

TABLE 3

In Vivo Wet Weight Bioassay Results
(DES-Stimulated Growth of Uteri)

| Experiment # | Assay | Dose per Mouse | Percent Growth Inhibition |
|---|---|---|---|
| 1 | immature mouse uterus | 800 ng | 18% |
| 2 | immature mouse uterus | 10 ng | 27% |
| 3 | immature mouse uterus | 100 μg | 14% |
| 4 | immature mouse uterus | 10 μg | 20% |
| 5 | immature mouse uterus | 1 μg | 22% |
| 6 | immature mouse uterus | 100 ng | 25% |
| 7 | immature mouse uterus | 10 ng | 25% |
| 8 | adult mouse uterus | 100 μg | 25% |
| 9 | adult mouse uterus | 100 ng | 22% |

TABLE 4

In Vivo Wet Weight Bioassay Results
(HC-Stimulated Growth of the Spleen)

| Experiment # | Assay | Dose per Mouse | Percent Growth Inhibition |
|---|---|---|---|
| 1* | immature mouse spleen | 100 μg | 24% |
| 2* | immature mouse spleen | 100 μg | 34% |
| 3 | immature mouse spleen | 100 μg | 67% |
| 4 | immature mouse spleen | 10.0 μg | 76% |
| 5 | immature mouse spleen | 1.0 μg | 100% |
| 6 | immature mouse spleen | 500 ng | 67% |

* These mice received 1.0 μg of HC instead of 0.5 μg.

TABLE 5

In Vivo Wet Weight Bioassay Results
(HCG-Stimulated Growth of the Ovary)

| Experiment # | Assay | Dose per Mouse | Percent Growth Inhibition |
|---|---|---|---|
| 1 | immature mouse ovary | 100 μg | 22% |
| 2 | immature mouse ovary | 10 μg | 94% |
| 3 | immature mouse ovary | 1 μg | 100% |
| 4 | immature mouse ovary | 500 ng | 67% |
| 5 | immature mouse ovary | 250 ng | 56% |
| 6 | immature mouse ovary | 125 ng | 50% |
| 7 | immature mouse ovary | 1 μg | 79% |
| 8 | immature mouse ovary | 100 ng | 70% |
| 9 | immature mouse ovary | 10 ng | 67% |
| 10 | adult mouse ovary | 10 μg | 50% |

TABLE 6

In Vivo Wet Weight Bioassay Results
(Estrogen-Stimulatd Growth of Uteri)

| Fragment SEQ ID NO: | Assay | Dose Per Mouse | Percent Growth Inhibition |
|---|---|---|---|
| 5 | immature mouse uterus | 10–100 ng | 38% |
| 6 | immature mouse uterus | 10–100 ng | 19% |
| 7 | immature mouse uterus | 10–100 ng | * |
| 2 | immature mouse uterus | 10–100 ng | 28% |
| 3 | immature mouse uterus | 10–100 ng | 20% |
| 4 | immature mouse uterus | 10–100 ng | 41% |

*no detectable growth inhibition

TABLE 7

In Vivo 6WI-1 Assay Results

| Peptide or Fragment SEQ ID NO: | Assay | Dose Per Mouse | Percent Growth Inhibition |
|---|---|---|---|
| 1 | adult mouse | 100 μg | 79% |
| 2 | adult mouse | 1000 μg | 30% |
| 3 | adult mouse | 1000 μg | 47% |
| 4 | adult mouse | 100 μg | 40% |
| 1[a] | adult mouse | 100 μg | 85% |
| 1 | immature mouse | 1000 μg | 49% |
| 2 | immature mouse | 1000 μg | 21% |
| 3 | immature mouse | 1000 μg | 42% |
| 4 | immature mouse | 1000 μg | 20% |
| 3/2[b] | immature mouse | 1000 μg | 48% |
| 4/3[c] | immature mouse | 1000 μg | 47% |

[a]1.1–4.0 × 10⁶ tumor cells were mixed with 100 μg of the peptide on day 1 and 100 μg of the mixture was injected into the test animal only on day 1.
[b,c]500 μg of each peptide fragment were mixed together and 1000 μg of the mixture was injected into the test animal on day 1 and every day for 15 days.

TABLE 8

In Vivo 6WI-1 Assay Results

| Peptide or Fragment SEQ ID NO: | Assay | Dose Per Mouse | Percent Growth Inhibition |
|---|---|---|---|
| 1 | adult mouse | 100 μg | 97% |
| 1[a] | adult mouse | 100 μg | 97% |
| 1 | immature mouse | 1000 μg | 57% |
| 3/2[b] | immature mouse | 1000 μg | 82% |

[a]0.3–1.0 × 10⁶ tumor cells were mixed with 100 μg of the peptide on day 1 and 100 μg of the mixture was injected into the test animal only on day 1.
[b]500 μg of each peptide fragment were mixed together and 1000 μg of the mixture was injected into the test animal on day 1 and every day for 15 days.

What is claimed is:

1. A method of inhibiting growth factor-stimulated growth of cells, said growth factor-stimulated growth being stimulated by a growth factor selected from the group consisting of estrogen, diethylstilbestrol, hydrocortisone, and human chorionic gonadotropin, said method comprising selecting a sample having cells therein capable of growth factor-stimulated growth, and contacting said sample with a peptide so as to inhibit growth factor-stimulated growth of said cells, wherein said peptide is a non-naturally occurring peptide having an amino acid sequence selected from the group consisting of SEQ ID NO:1 and SEQ ID NO:8.

2. A method of inhibiting growth factor-stimulated growth of cells, said growth factor-stimulated growth being stimulated by a growth factor selected from the group consisting of estrogen, diethylstilbestrol, hydrocortisone, and human chorionic gonadotropin, said method comprising selecting a sample having cells therein capable of growth factor-stimulated growth, and contacting said sample with a peptide so as to inhibit growth factor-stimulated growth of said cells, wherein said peptide is a non-naturally occurring peptide having an amino acid sequence selected from the group consisting of SEQ ID NO:2, SEQ ID NO:3, SEQ ID NO:4, SEQ ID NO:5, SEQ ID NO:6, SEQ ID NO:7, SEQ ID NO:9, SEQ ID NO:10, and SEQ ID NO:11.

3. The method of claim 1 wherein said growth factor is estrogen and said cells are uterus cells.

4. The method of claim 1 wherein said growth factor is diethylstilbestrol and said cells are uterus cells.

5. The method of claim 1 wherein said growth factor is hydrocortisone and said cells are spleen cells.

6. The method of claim 1 wherein said growth factor is human chorionic gonadotropin and said cells are ovary cells.

7. The method of claim 1 wherein said peptide is methylated, amidated, or biotinylated.

8. The method of claim 2 wherein said growth factor is estrogen and said cells are uterus cells.

9. The method of claim 2 wherein said growth factor is diethylstilbestrol and said cells are uterus cells.

10. The method of claim 2 wherein said growth factor is hydrocortisone and said cells are spleen cells.

11. The method of claim 2 wherein said growth factor is human chorionic gonadotropin and said cells are ovary cells.

12. The method of claim 2 wherein said peptide is methylated, amidated, or biotinylated.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 34 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:1:

```
Leu  Ser  Glu  Asp  Lys  Leu  Leu  Ala  Cys  Gly  Glu  Gly  Ala  Ala  Asp  Ile
 1                  5                            10                       15

Ile  Ile  Gly  His  Leu  Cys  Ile  Arg  His  Glu  Met  Thr  Pro  Val  Asn  Pro
                    20                       25                      30

Gly  Val
```

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:2:

Leu Ser Glu Asp Lys Leu Leu Ala Cys Gly Glu Gly
1               5                   10

( 2 ) INFORMATION FOR SEQ ID NO:3:

( i ) SEQUENCE CHARACTERISTICS:
        ( A ) LENGTH: 14 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:3:

Ala Ala Asp Ile Ile Ile Gly His Leu Cys Ile Arg His Glu
1               5                   10

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:4:

Glu Met Thr Pro Val Asn Pro Gly
1               5

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:5:

His Glu Met Thr Pro Val Asn Pro Gly Val
1               5                   10

( 2 ) INFORMATION FOR SEQ ID NO:6:

( i ) SEQUENCE CHARACTERISTICS:
        ( A ) LENGTH: 19 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:6:

Leu Leu Ala Cys Gly Glu Gly Ala Ala Asp Ile Ile Ile Gly His Leu
1               5                   10                  15

Cys Ile Arg ( 2 ) INFORMATION FOR SEQ ID NO:7:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: linear (i i) MOLECULE TYPE: peptide (x i) SEQUENCE DESCRIPTION: SEQ ID NO:7:

Leu Ser Glu Asp Lys
1               5

(2) INFORMATION FOR SEQ ID NO:8:

(i) SEQUENCE CHARACTERISTICS:
        (A) LENGTH: 34 amino acids
        (B) TYPE: amino acid
        (C) STRANDEDNESS: Not Relevant
        (D) TOPOLOGY: linear (i i) MOLECULE TYPE: peptide (x i) SEQUENCE DESCRIPTION: SEQ ID NO:8:

Leu Ser Glu Asp Lys Leu Leu Ala Xaa Gly Glu Gly Ala Ala Asp Ile
1               5                   10                  15

Ile Ile Gly His Leu Xaa Ile Arg His Glu Met Thr Pro Val Asn Pro
            20              25                  30

Gly Val (2) INFORMATION FOR SEQ ID NO:9:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (i i) MOLECULE TYPE: peptide (x i) SEQUENCE DESCRIPTION: SEQ ID NO:9:

Leu Ser Glu Asp Lys Leu Leu Ala Xaa Gly Glu Gly
1               5                   10

(2) INFORMATION FOR SEQ ID NO:10:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: linear (i i) MOLECULE TYPE: peptide (x i) SEQUENCE DESCRIPTION: SEQ ID NO:10:

Ala Ala Asp Ile Ile Ile Gly His Leu Xaa Ile Arg His Glu
1               5                   10

(2) INFORMATION FOR SEQ ID NO:11:

(i) SEQUENCE CHARACTERISTICS:
        (A) LENGTH: 19 amino acids
        (B) TYPE: amino acid
        (C) STRANDEDNESS: Not Relevant
        (D) TOPOLOGY: linear (i i) MOLECULE TYPE: peptide (x i) SEQUENCE DESCRIPTION: SEQ ID NO:11:

Leu Leu Ala Xaa Gly Glu Gly Ala Ala Asp Ile Ile Ile Gly His Leu
1               5                   10                  15

Xaa Ile Arg